US012181382B2

(12) United States Patent
Jin et al.

(10) Patent No.: US 12,181,382 B2
(45) Date of Patent: Dec. 31, 2024

(54) MICRO CORE-DRILLING TESTING SYSTEM FOR HIGH-PRESSURE ENVIRONMENT

(71) Applicant: HUNAN UNIVERSITY OF SCIENCE AND TECHNOLOGY, Xiangtan (CN)

(72) Inventors: Yongping Jin, Xiangtan (CN); Xiaobin He, Xiangtan (CN); Youduo Peng, Xiangtan (CN); Ping Liu, Xiangtan (CN)

(73) Assignee: HUNAN UNIVERSITY OF SCIENCE AND TECHNOLOGY, Xiangtan (CN)

( * ) Notice: Subject to any disclaimer, the term of this patent is extended or adjusted under 35 U.S.C. 154(b) by 362 days.

(21) Appl. No.: 17/941,235

(22) Filed: Sep. 9, 2022

(65) Prior Publication Data
US 2023/0003619 A1     Jan. 5, 2023

(30) Foreign Application Priority Data

Aug. 25, 2022   (CN) .......................... 202211036974.6

(51) Int. Cl.
*G01N 1/08*      (2006.01)
*E21B 7/12*      (2006.01)
*E21B 41/00*     (2006.01)
*G01N 33/24*     (2006.01)

(52) U.S. Cl.
CPC ................ *G01N 1/08* (2013.01); *E21B 7/12* (2013.01); *G01N 33/24* (2013.01); *E21B 41/0007* (2013.01)

(58) Field of Classification Search
CPC ........................... G01N 1/08; G01N 2001/085
See application file for complete search history.

(56) References Cited

U.S. PATENT DOCUMENTS

2023/0094439 A1*  3/2023  Wei ................... G01N 33/24
                                                           73/7

FOREIGN PATENT DOCUMENTS

| CN | 109667541 A | * | 4/2019 | ............ E21B 47/00 |
| CN | 110185383 A | * | 8/2019 | ........... E21B 15/003 |
| CN | 110454105 A | * | 11/2019 | ............ E21B 25/04 |
| CN | 108952659 B | * | 6/2020 | ........... E21B 43/164 |
| CN | 112377165 A | * | 2/2021 | ............ E21B 43/26 |
| CN | 113137223 A | * | 7/2021 | |
| CN | 113186994 A | * | 7/2021 | ............ E02D 19/06 |
| CN | 113216933 A | * | 8/2021 | ............ E21B 23/04 |
| CN | 214576985 U | | 11/2021 | |
| CN | 110220740 B | * | 7/2022 | ............... G01N 1/08 |
| KR | 20140129586 A | * | 11/2014 | |
| KR | 20140137275 A | * | 12/2014 | |
| KR | 20150000163 A | * | 1/2015 | |

(Continued)

*Primary Examiner* — Herbert K Roberts (57) ABSTRACT

A micro core-drilling testing system for high-pressure environment, including: a pressure chamber, a micro core-drilling testing platform and a control device. The micro core-drilling testing platform includes a lower tray, a middle tray, a hydraulic system, a stroke cylinder, a rock sample plate, a rock sample block, a pressure compensation device and a drilling rig. The drilling rig is configured to carry out core-drilling operation. The hydraulic system is configured to provide power for the drilling rig. The pressure compensation device is configured to balance the pressure inside the pressure chamber and the hydraulic system.

10 Claims, 6 Drawing Sheets

(56) References Cited

FOREIGN PATENT DOCUMENTS

| KR | 20150000167 | A | * | 1/2015 |
| KR | 20150002089 | A | * | 1/2015 |
| KR | 20150002090 | A | * | 1/2015 |
| KR | 20150001773 | U | * | 5/2015 |
| KR | 20150063752 | A | * | 6/2015 |
| KR | 20150127446 | A | * | 11/2015 |

* cited by examiner

MICRO CORE-DRILLING TESTING SYSTEM FOR HIGH-PRESSURE ENVIRONMENT

CROSS-REFERENCE TO RELATED APPLICATIONS

This application claims the benefit of priority from Chinese Patent Application No. 202211036974.6 filed on Aug. 25, 2022. The content of the aforementioned application, including any intervening amendments thereto, is incorporated herein by reference in its entirety.

TECHNICAL FIELD

This application relates to marine drilling rigs, and more particularly to a micro core-drilling testing system for high-pressure environment.

BACKGROUND

With the advancement of science and technology, the demand for resources is continuously increasing, and the resource shortage becomes increasingly serious. More and more attention has been paid to the exploitation of marine resources. At present, due to the advantages of high coring efficiency, small sampling disturbance, strong maneuverability, easy operation and strong ship adaptability, the core sampling rig has become an indispensable technical tool for deep seafloor exploration. During the deep seafloor exploration, the core sampling rig will be inevitably affected by the ultra-high pressure seafloor environment. A 100-m increase in the depth will be accompanied by a 1-MPa increase in the pressure on the core sampling rig. In order to explore the drilling and coring rules of the core sampling rig under deep-sea high-pressure environment, a micro core-drilling testing platform for high-pressure environment is designed.

SUMMARY

An objective of this application is to provide a micro core-drilling testing system for high-pressure environment to explore the drilling and coring rules under deep-sea high-pressure environment, so as to provide reference for the subsequent deep-sea drilling project.

Technical solutions of this application are described as follows.

This application provides a micro core-drilling testing system under high-pressure environment, comprising:
 a pressure chamber;
 a micro core-drilling testing platform; and
 a control device;
 wherein the micro core-drilling testing platform is arranged in the pressure chamber; the micro core-drilling testing platform comprises a lower tray, a middle tray, a hydraulic system, a stroke cylinder, a rock sample plate, a rock sample block, a pressure compensation device and a drilling rig; the middle tray is arranged on the lower tray through a plurality of first upright posts; the hydraulic system and the pressure compensation device are arranged on the lower tray; the rock sample plate is supported on the plurality of first upright posts; the rock sample block is fixed on the rock sample plate; the middle tray is provided with a first guide column; the first guide column is vertically provided with a guide chute; the drilling rig is installed on a slide rest; the slide rest is arranged in the guide chute; a lower end of the stroke cylinder is hingedly connected to the middle tray or a bottom of the first guide column, and an upper end of the stroke cylinder is hingedly connected to the slide rest; a drill pipe of the drilling rig is located directly above the rock sample block; the middle tray is provided with a first drill pipe hole corresponding to the drill pipe; the drilling rig, the pressure compensation device and the stroke cylinder are connected to the hydraulic system; and the hydraulic system is connected to the control device.

In an embodiment, the micro core-drilling testing platform further comprises an upper tray; and the upper tray is arranged on the middle tray through a plurality of second upright posts.

In an embodiment, the rock sample block is fixed on the rock sample plate through four clamps; each of the four clamps comprises a bottom plate, a side plate and a reinforcing rib; the bottom plate is fixed on the rock sample plate; the side plate is perpendicularly connected to the bottom plate; the reinforcing rib is provided between the bottom plate and the side plate; and a side surface of the side plate clings to a side surface of the rock sample block.

In an embodiment, a water inlet is provided on a cover at a top of the pressure chamber; the water inlet is connected to an outlet of a pump through a water pipe; an inlet of the pump is connected to a water tank through a pipeline; a top surface of the cover is provided with four first watertight connectors, and a bottom surface of the cover is provided with four second watertight connectors; the four first watertight connectors are respectively electrically connected with the four second watertight connectors; the four second watertight connectors are respectively connected to a temperature sensor, a pressure sensor, a camera and an illumination device; the four first watertight connectors are connected to the control device through a collection device.

In an embodiment, the bottom of the first guide column is provided with a base; the base is screwedly fixed on the middle tray; the lower end of the stroke cylinder is hingedly connected to the base; the base is provided with a second drill pipe hole corresponding to the first drill pipe hole on the middle tray; and a drill bushing is provided at the second drill pipe hole.

In an embodiment, the drilling rig comprises a first hydraulic motor, a power head spindle, a jettisoning shaft, a ratchet wheel and a power head housing; the first hydraulic motor is fixedly provided on a top of the power head housing; the power head housing is fixedly connected to the slide rest; the power head spindle is supported by a first bearing provided inside the power head housing; an upper end of the power head spindle is connected to an output shaft of the first hydraulic motor; the ratchet wheel is fixed on the power head spindle by key joint;

the power head housing is provided with a screw-off cylinder corresponding to the ratchet wheel; a pawl groove on a side of a piston rod of the screw-off cylinder is hingedly connected to a pawl through a pawl pin; a torsion spring is provided on the pawl pin; one end of the torsion spring is connected to the pawl, and the other end of the torsion spring is connected to the piston rod of the screw-off cylinder; the pawl is in fit with the ratchet wheel to form a ratchet wheel-pawl mechanism; the screw-off cylinder is connected to the hydraulic system; the power head spindle is sleevedly provided with a jettisoning shaft control sleeve; the jettisoning shaft control sleeve is located inside the power head housing; two hydraulic cavities are formed between the jettisoning shaft control sleeve and an inner wall of the power head housing; the two hydraulic cavities are respectively connected to two oil ports on the power head housing;

the two oil ports are respectively connected to the hydraulic system to control the jettisoning shaft control sleeve to move along an axis of the power head housing; the jettisoning shaft is arranged in a center hole of the power head spindle; the power head spindle is provided with a plurality of through holes; the plurality of through holes are located in the same plane; a steel ball is provided in each of the plurality of through holes; the jettisoning shaft is provided with a plurality of first grooves respectively corresponding to the plurality of through holes; an upper end surface of each of the plurality of first grooves is a tapered surface; an lower end of the jettisoning shaft control sleeve is provided with a plurality of second grooves, wherein each of the plurality of second grooves is annular; the jettisoning shaft control sleeve is configured to press steel balls respectively into the plurality of first grooves, so as to enable connection of the jettisoning shaft with the power head spindle; when the plurality of second grooves are respectively aligned with the plurality of through holes, the jettisoning shaft is separated from the power head spindle; a lower end of the jettisoning shaft is connected to the drill pipe; and a coring sleeve is provided inside the drill pipe.

In an embodiment, two first sealing rings are arranged between an outer side of the jettisoning shaft control sleeve and an inner side of the power head housing; the bearing comprises a first bearing and a second bearing; an upper end of the power head housing is provided with the first bearing, and a lower end of the power head housing is provided with the second bearing; the first bearing is positioned by an adjusting ring and the ratchet wheel; the adjusting ring is located above the first bearing; an upper end of the adjusting ring is positioned through a lower end of the hydraulic motor; the second bearing is positioned by a power head end cover and a thrust ring; the thrust ring is located inside the power head housing; and an upper end of the thrust ring is positioned by a shaft shoulder on an inner side wall of the power head housing.

In an embodiment, a second sealing ring is arranged between an inner hole of the thrust ring and the jettisoning shaft control sleeve; a third sealing ring is arranged between an outer side of the thrust ring and the power head housing; the second sealing ring and the third sealing ring are both O-shaped; and three oil seals are arranged between the jettisoning shaft and an inner hole of the power head end cover; the pressure compensation device comprises a corrugated pipe, a spring, an upper pressure plate and a base; one end of the corrugated pipe is fixed on the upper pressure plate, and the other end of the corrugated pipe is fixed on the base; the spring is provided inside the corrugated pipe; one end of the spring is connected to the base, and the other end of the spring is connected to the upper pressure plate; the base is provided with a plurality of second guide columns; an axis of each of the plurality of the second guide columns is in parallel to an axis of the corrugated pipe; the upper pressure plate is provided with a plurality of guide holes; the plurality of guide holes are sleevedly provided on the plurality of second guide columns, respectively; and an oil port on the base is communicated with the hydraulic system.

In an embodiment, the lower end of the jettisoning shaft is provided with a radial water inlet and an axial water inlet; the radial water inlet is located between two oil seals of the three oil seals; the radial water inlet is communicated with the axial water inlet; the radial water inlet is communicated with a water inlet hole on the power head end cover; a flushing joint is provided at the water inlet hole of the power head end cover; a water pump and a second hydraulic motor are fixed on the rock sample plate; an oil suction port and an oil return port of the second hydraulic motor are connected to the hydraulic system through oil pipes; an output shaft of the second hydraulic motor is connected to the water pump, and a water outlet of the water pump is connected to the flushing joint; and a water suction port of the water pump is connected to a filter through a water pipe.

In an embodiment, the slide rest comprises a main sliding plate, two reinforcing plates, a supporting plate, and a cover plate; the supporting plate is perpendicularly connected to the main sliding plate; the two reinforcing plates are provided between the supporting plate and the main sliding plate; one of the two reinforcing plates is located at a first end of the supporting plate, and the other of the two reinforcing plates is located at a second end of the supporting plate; the supporting plate is provided with a mounting hole; the first hydraulic motor is mounted in the mounting hole; the power head housing is screwedly connected to the main sliding plate; the cover plate is screwedly provided on a surface of the main sliding plate away from the supporting plate; the cover plate is screwedly provided with a sliding connector; and the sliding connector passes through the guide chute to be hingedly connected to a joint of a piston rod of the stroke cylinder.

Compared with the prior art, this application has the following beneficial effects.

1. Regarding the testing system provide herein, the seawater is taken as a working medium, and the high-pressure simulation chamber is capable of simulating the deep-sea high-pressure environment, such that the drilling and coring process under different pressure environments can be simulated.

2. This application is capable of simulating the drilling test of diamond drill bits of different specifications by adopting drill pipe connecting pipes with different specifications.

3. In this application, the hydraulic system is taken as a power source, and the drilling pressure and the rotational speed of the drill bit can be adjusted within a wide range.

DETAILED DESCRIPTION OF EMBODIMENTS

This application will be described in detail below with reference to the accompanying drawings and embodiments.

Figure 1:
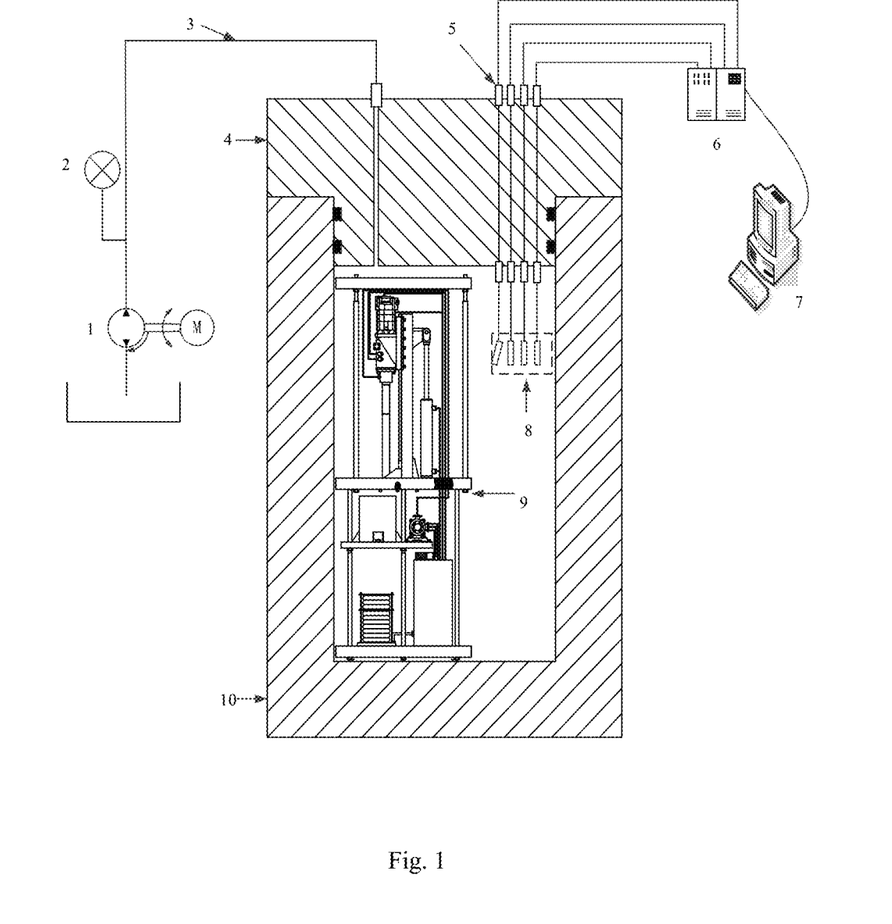
FIG. 1 structurally shows a micro core-drilling testing system according to an embodiment of this application.

Referring to an embodiment shown in FIG. 1, a micro core-drilling testing system for high-pressure environment is provided herein, which includes a pressure chamber 10, a micro core-drilling testing platform 9, a collection device 6, a control device 7, a pressure sensor, a temperature sensor, an illumination device and a camera. A water inlet is provided on a cover 4 which is provided at a top of the pressure chamber 10. The water inlet is connected to an outlet of a high-pressure pump 1 through a high-pressure water pipe 3. An inlet of the high-pressure pump 1 is connected to a water tank through a pipeline, and the water tank is filled with seawater. Top and bottom surfaces of the cover 4 are each provided with four watertight connectors 5. The four watertight connectors on the top surface are respectively electrically connected with the four watertight connectors on the bottom surface. The four watertight connectors on the bottom surface of the cover 4 are respectively connected to the temperature sensor, the pressure sensor, the camera and the illumination device. The four watertight connectors on the top surface of the cover 4 are connected to the control device 7 through the collection device 6. The micro core-drilling testing platform 9 is arranged in the pressure chamber 10.

As shown in FIGS. 2-8, the micro core-drilling testing platform 9 includes a lower tray 912, a middle tray 905, an upper tray 901, a hydraulic system 909, a stroke cylinder 90309, a rock sample plate 908, a rock sample block 906, a pressure compensation device 910 and a drilling rig 903. The middle tray 905 is arranged on the lower tray 912 through six first upright posts, and the upper tray 901 is arranged on the middle tray 905 through four second upright posts 902.

The hydraulic system 909 and the pressure compensation device 910 are arranged on the lower tray 912. The rock sample plate 908 is supported on the four first upright posts at a left side. The pressure compensation device 910 includes a corrugated pipe, a spring, an upper pressure plate and a base. one end of the corrugated pipe is fixed on the upper pressure plate, and the other end of the corrugated pipe is fixed on the base. The spring is provided inside the corrugated pipe; one end of the spring is connected to the base, and the other end of the spring is connected to the upper pressure plate. The base is provided with a plurality of second guide columns; an axis of each of the plurality of the second guide columns is in parallel to an axis of the corrugated pipe. The upper pressure plate is provided with a plurality of guide holes. The plurality of guide holes are sleevely provided on the plurality of second guide columns, respectively. An oil port on the base is communicated with the hydraulic system. When the pressure in the pressure chamber 10 is higher than the pressure in the hydraulic system 909, the volume of the corrugated pipe decreases, and the oil in the corrugated pipe enters the hydraulic system 909 through the oil port on the base to compensate the pressure of the hydraulic system, such that an equilibrium between the pressure in the pressure chamber 10 and the pressure in the hydraulic system 909 is achieved. The rock sample block 906 is fixed on the rock sample plate 908 through four clamps 907. Each of the four clamps 907 includes a bottom plate, a side plate and a reinforcing rib. The bottom plate is fixed on the rock sample plate 908, and the side plate is perpendicularly connected to the bottom plate. The reinforcing rib is arranged between the bottom plate and the side plate. A side surface of the side plate clings to a side surface of the rock sample block 906. A right side of the rock sample plate 908 is fixedly provided with a water pump 914 and a second hydraulic motor 915. An oil suction port and an oil return port of the second hydraulic motor 915 are connected to the hydraulic system 909 through oil pipes.

An output shaft of the second hydraulic motor 915 is connected to the water pump 914. The bottom of a guide column 90313 is provided with a base, and the base is screwedly fixed on the middle tray 905. The guide column 90313 is vertically provided with a guide chute. The drilling rig 903 is installed on a slide rest 913. A lower end of the stroke cylinder 90309 is hingedly connected to the middle tray or a bottom of the guide column 90313 through a first pin 90312 of the stroke cylinder 90309. An upper end of the stroke cylinder 90309 is screwedly connected to a joint 90304 of a piston rod of the stroke cylinder 90309. The joint 90304 of a piston rod of the stroke cylinder is hingedly connected to the slide rest 913 through a second pin 90302. A drill pipe 90310 is located directly above the rock sample block 906. The middle tray 905 is provided with a first drill pipe hole corresponding to the drill pipe 90310. The drilling rig 903, the pressure compensation device 910 and the stroke cylinder 90309 are respectively connected to the hydraulic system 909. The hydraulic system 909 is connected to the control device 907. The base of the guide column is provided with a second drill pipe hole corresponding to the first drill pipe hole. A drill bushing 90315 is provided at the second drill pipe hole through screws 90314.

As shown in FIGS. 3-6, the drilling rig 903 includes a first hydraulic motor 90301, a power head spindle 90332, a connecting pipe 90308, the drill pipe 90310, a coring sleeve pipe 90311, a jettisoning shaft 90327, a ratchet wheel 90318 and a power head housing 90306. The first hydraulic motor 90301 is fixedly provided on a support plate 90333 of the slide rest 913. The support plate 90333 is fixedly provided on a top of the power head housing 90306. The coring sleeve pipe 90311 is installed inside the drill pipe 90310. The slide rest 913 includes a main sliding plate 90305, a reinforcing plate 90335, a supporting plate 90333 and a cover plate 90336 of the slide rest 913. The supporting plate 90333 is perpendicularly connected to the main sliding plate 90305. Two reinforcing plates 90335 are provided between the supporting plate 90333 and the main sliding plate 90305. One of the two reinforcing plates 90335 is located at a first end of the supporting plate 90333, and the other of the two reinforcing plates is located at a second end of the supporting plate 90333. The supporting plate 90333 is provided with mounting holes. The first hydraulic motor 90301 is installed in the mounting holes. The power head housing 90306 is connected to the main sliding plate 90305 through screws. The cover plate 90336 of the slide rest 913 is screwedly mounted on a surface of the main sliding plate 90305 away from the supporting plate 90333. The cover plate 90336 of the slide rest 913 is screwedly provided with a sliding connector 90303. The sliding connector 90303 passes through the guide chute to be hingedly connected to the joint 90304 of a piston rod of the stroke cylinder. The power head spindle 90332 is supported by two bearings 90325 provided inside the power head housing 90306. The two bearings 90325 comprises a first bearing and a second bearing. The first bearing is provided at an upper end of the power head housing 90306, and the second bearing is provided at a lower end of the power head housing 90306. The first bearing is positioned by an adjusting ring 90316 and the ratchet wheel 90318. The adjusting ring 90316 is located above the first bearing. An upper end of the adjusting ring 90316 is positioned through a lower end of the hydraulic motor 90301. The second bearing is positioned by a power head end cover 90326 and a thrust ring 90324. The thrust ring 90324 is located inside the power head housing

90306. An upper end of the thrust ring 90324 is positioned by a shaft shoulder on an inner side wall of the power head housing.

An upper end of the power head spindle 90332 is in key connection to an output shaft of the first hydraulic motor. The ratchet wheel 90318 is fixed on the power head spindle 90332 by key joint. The power head housing 90306 is provided with a screw-off cylinder 90341 corresponding to the ratchet wheel 90318. A piston 90319 of the screw-off cylinder 90341 is cylindrical. An oil cylinder cover of the screw-off cylinder 90341 is provided with an oil pipe interface 90340. The oil pipe interface 90340 is connected to the hydraulic system through a pipe. A pawl groove on a side wall of a piston rod 90319 of the screw-off cylinder 90341 is hingedly connected to a pawl 90320 through a pawl pin 90337. A torsion spring 90338 is provided on the pawl pin 90337. One end of the torsion spring 90338 is connected to the pawl, and the other end of the torsion spring 90338 is connected to the piston rod of the screw-off cylinder. The pawl 90320 is in fit with the ratchet wheel 90318 to form a ratchet wheel-pawl mechanism. When the drilling rod is stuck, the screw-off cylinder 90341 moves to allow the power head spindle 90332 rotate, thereby driving the unstuck part of the drill rod to rotate, so as to separate the stuck part of the drilling rod.

The power head spindle 90332 is sleevedly provided with the jettisoning shaft control sleeve 90331. The jettisoning shaft control sleeve 90331 is located inside the power head housing 90306. Two hydraulic cavities are formed between the jettisoning shaft control sleeve 90331 and an inner wall of the power head housing 90306. The two hydraulic cavities are respectively communicated to two oil ports 917 on the power head housing 90306. The two oil ports are respectively connected to the hydraulic system 909 to control the jettisoning shaft control sleeve 90331 to move along an axis of the power head housing 90306.

The jettisoning shaft 90327 is arranged in a center hole of the power head spindle 90332. The power head spindle 90332 is provided with a plurality of through holes. The plurality of through holes are located in the same plane. A steel ball is provided in each of the plurality of through holes. the jettisoning shaft 90327 is provided with a plurality of first grooves respectively corresponding to the plurality of through holes. An upper end surface of each of the plurality of first grooves is a tapered surface. An lower end of the jettisoning shaft control sleeve 90331 is provided with a plurality of second grooves, where each of the plurality of second grooves is annular. The jettisoning shaft control sleeve 90331 is configured to press steel balls respectively into the plurality of first grooves, so as to enable connection of the jettisoning shaft 90327 with the power head spindle 90332. When the plurality of second grooves are respectively aligned with the plurality of through holes, the jettisoning shaft 90327 is separated from the power head spindle 90332. A lower end of the jettisoning shaft 90327 is connected to the connecting pipe 90308 through cross recessed countersunk head screws 90307. A lower end of the connecting pipe 90308 is in threaded connection with the drill pipe 90310. A first sealing ring 90321 and a second sealing ring 90322 are arranged between an outer side of the jettisoning shaft control sleeve 90331 and an inner side of the power head housing 90306. A third sealing ring 90330 is arranged between an inner hole of the thrust ring 90324 and the jettisoning shaft control sleeve 90331. A fourth sealing ring 90329 is arranged between an outer side of the thrust ring 90324 and the power head housing 90306. The third sealing ring and the fourth sealing ring are both O-shaped.

Three oil seals 90328 are arranged between the jettisoning shaft 90327 and an inner hole of the power head end cover 90326. The lower end of the jettisoning shaft 90327 is provided with a radial water inlet and an axial water inlet. The radial water inlet is located between two oil seals of the three oil seals 90327. The radial water inlet is communicated with the axial water inlet. The radial water inlet is communicated with a water inlet hole on the power head end cover. A flushing joint 918 is provided at the water inlet hole of the power head end cover. An water outlet of the water pump 914 is connected to the flushing joint 918, and a water suction port of the water pump is connected to a filter 916 through water pipes. When the drilling rod is drilling, water is fed into the drill rod through the water pump.

In this embodiment, taking the deep-ocean pressure of 12,000 m as an example, how the micro core-drilling testing system performs the drilling and coring test is specifically described as follows.

Figure 2:
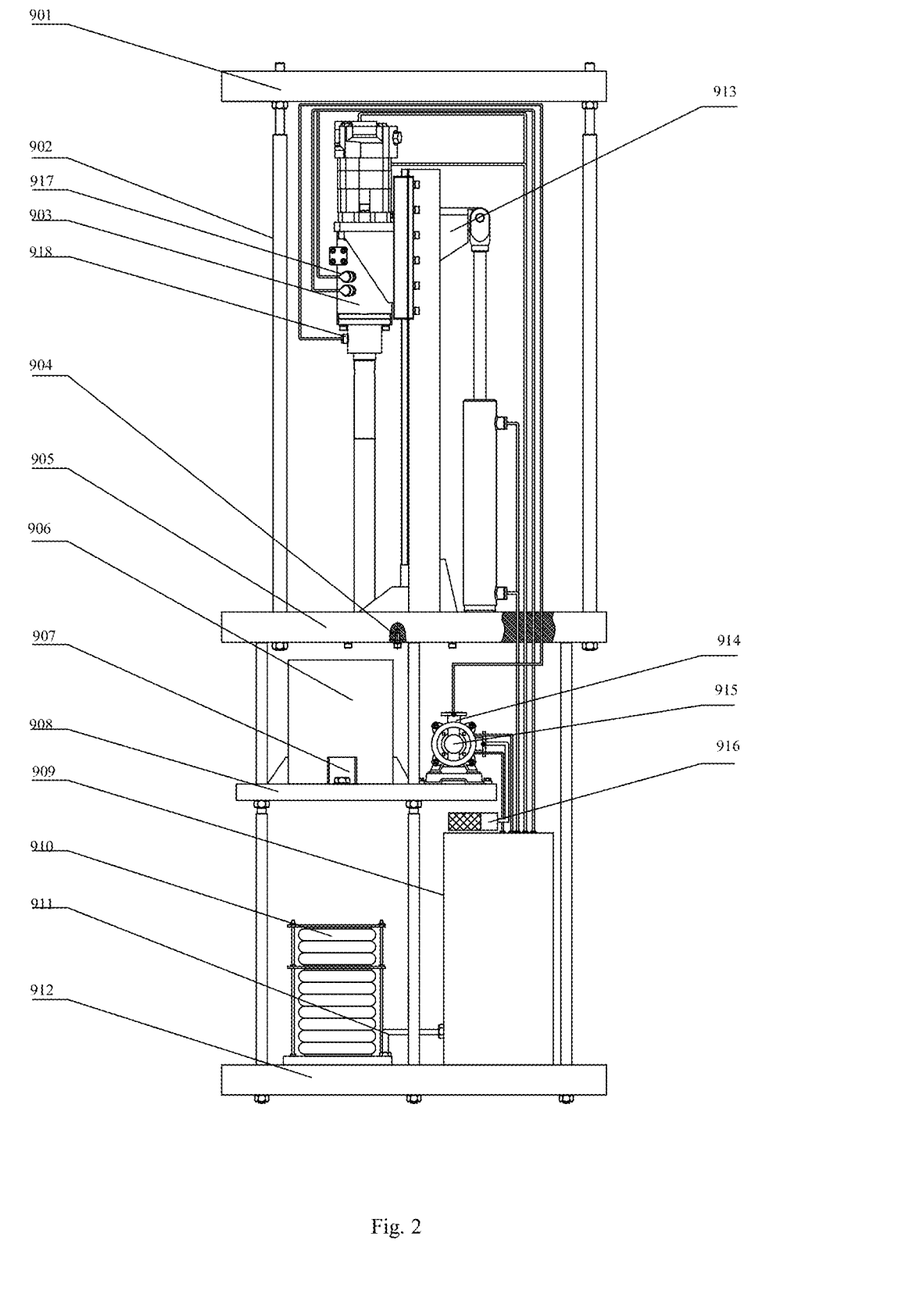
FIG. 2 is a structural diagram of a micro core-drilling testing system according to an embodiment of this application.
Figure 3:
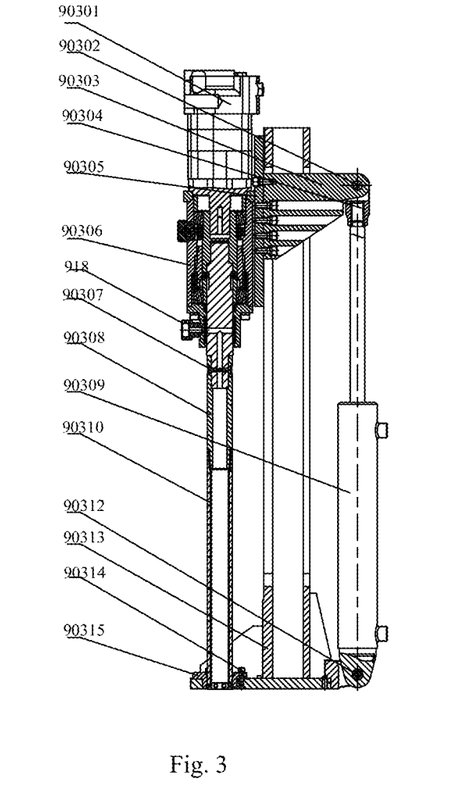
FIG. 3 depicts an overall structure of a drilling rig according to an embodiment of this application.
Figure 4:
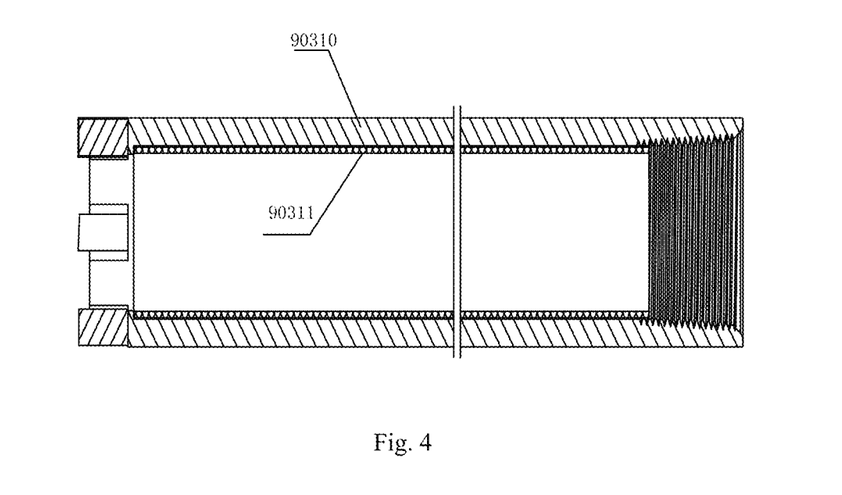
FIG. 4 is a sectional view of a drill pipe according to an embodiment of this application.

After completing the test preparation work, a diamond drilling bit is installed at a front end of the drill pipe 90310 of the micro-drilling rig as required. A rock sample block 906 is fixed on the rock sample plate 908. The overall installation of the testing platform 9 provided herein is checked, and then transferred to the pressure chamber. After that, the testing platform is well fixed to prevent generating large vibrations in use. The high-pressure pump 1 is started to pressurize the pressure chamber 10, and stop the pressurization when the value of the pressure gauge 2 reaches 120 MPa. During the pressurization process, the pressure compensation device 910 performs pressure compensation on the hydraulic system 909, such that the pressure difference between the inside and outside of the entire hydraulic system is basically equal to zero.

Figure 5:
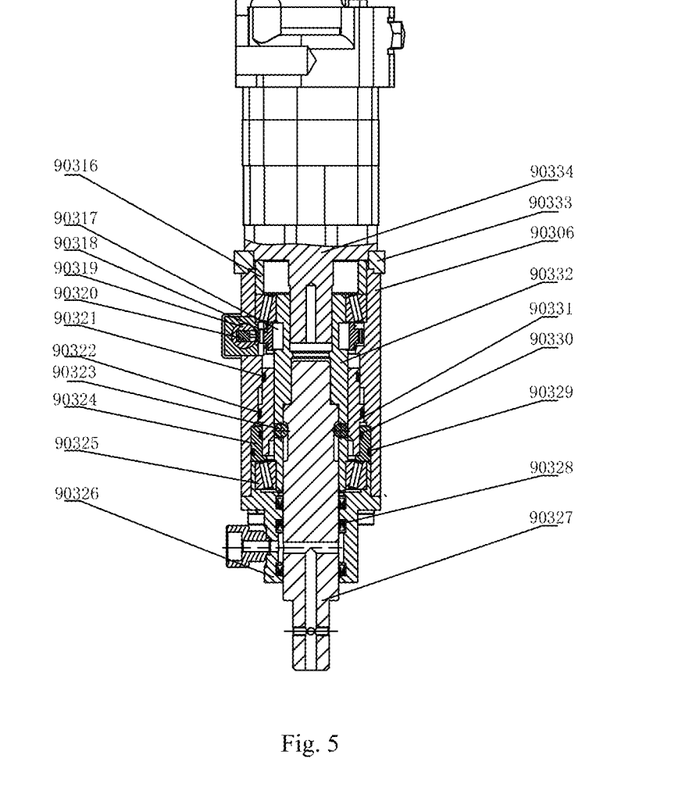
FIG. 5 is a sectional view of a power head housing according to an embodiment of this application.
Figure 6:
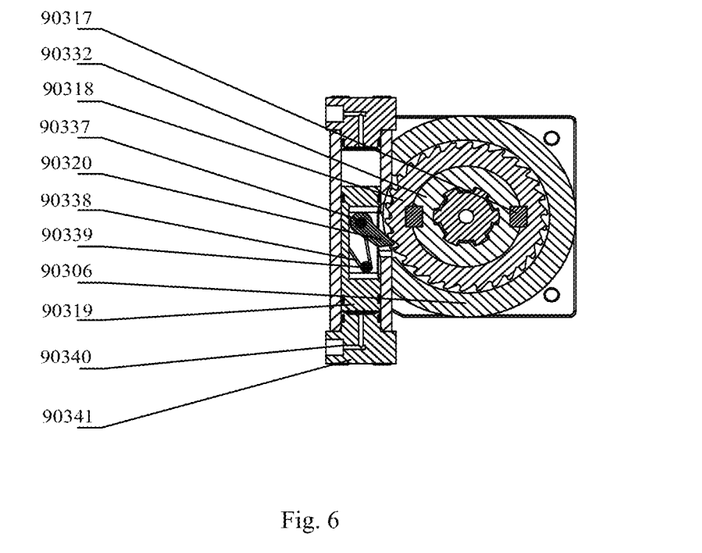
FIG. 6 is a cutaway view of a rachet wheel mechanism according to an embodiment of this application.
Figure 7:
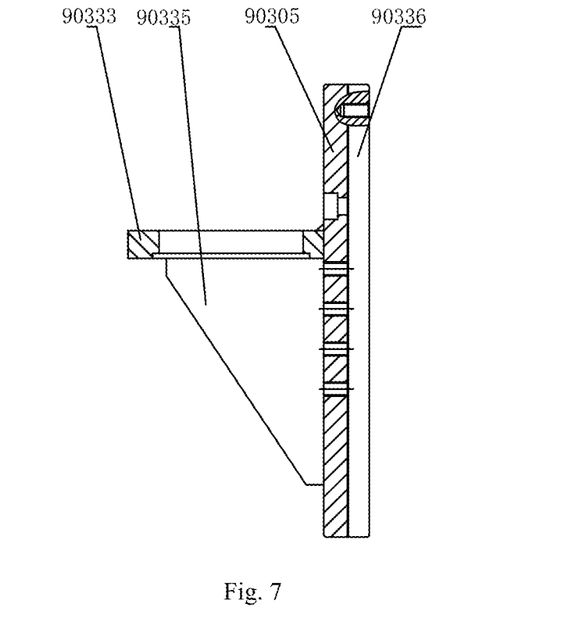
FIG. 7 a front view of a slide rest of the drilling rig according to an embodiment of this application.
Figure 8:
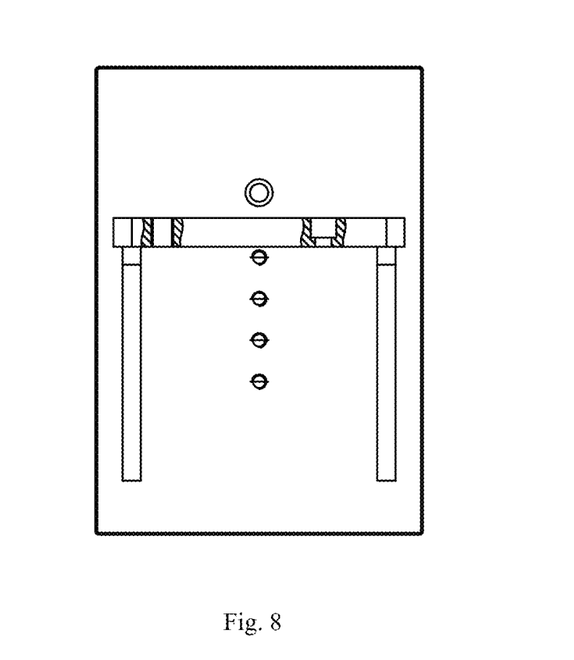
FIG. 8 is a left side view of the slide rest according to an embodiment of this application.
Figure 9:
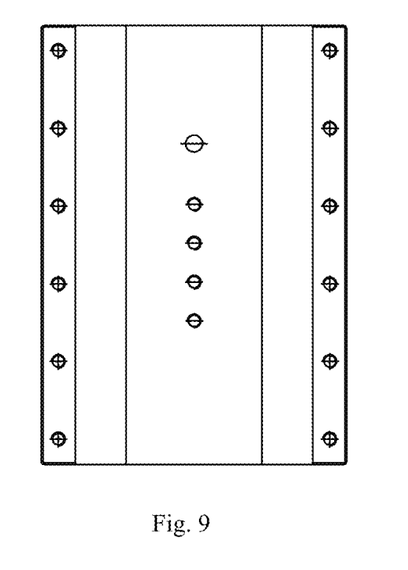
FIG. 9 is a right side view of the slide rest according to an embodiment of this application.

In the test, as shown in FIGS. 5-6, the jettisoning shaft 90327 is fixed with the power head spindle 90332 along an axial direction by the steel ball 90323 and transmits the force along the axial direction. The lower end of the jettisoning shaft 90327 is connected to the connecting pipe 90308 through the cross recessed countersunk head screw 90307. A lower end of the connecting pipe 90308 is threadedly connected with the drill pipe 90311. When the drilling is performed under normal circumstances, the rotary motion and torque output by the first hydraulic motor 90301 are transmitted to the drill pipe 90311 through the power head spindle 90332 and the jettisoning shaft 90327, so as to achieve the drilling into the rock formation. At the same time, the pressure and temperature variations caused by the drilling process are transmitted to the data acquisition system 6 through the sensor.

When the drill pipe 90310 is required to be jettisoned in the event of an accident, high-pressure hydraulic oil is injected into the annular oil cavity at the lower part of the jettisoning shaft control sleeve 90331 through the lower oil port of the oil port 917, and the oil return in the annular oil cavity on the upper part of the jettisoning shaft control sleeve 90331. The jettisoning shaft control sleeve 90331 is configured to move upwards. Because a second groove is provided on the lower part of the jettisoning shaft control sleeve 90331, when the second groove on the jettisoning shaft control sleeve 90331 is aligned with the steel ball 90323, the steel ball 90323 is gradually loosened. Due to the taper effect of the through hole of the power head spindle 90332 where the steel ball 90323 is provided, the steel ball 90323 is configured to automatically move toward an outer surface of the power head spindle 90332 due to the taper effect of the through hole on the power head spindle 90332 where the steel ball 90323 is located until the steel ball 90323 fails to withstand the step of the jettisoning shaft 90327, such that the jettisoning shaft 90327 enables free separation, and the jettisoning shaft 90327 and the drill pipe connected to the jettisoning shaft 90327 are both jettisoned.

Referring to an embodiment shown in FIG. 6, the piston of the screw-off cylinder 90341 is cylindrical. The side of the screw-off cylinder 90341 is provided with a pawl groove, where the pawl groove is rectangular. The pawl 90320 is installed on the pawl groove provided on the side of the screw-off cylinder 90341, and configured to be ejected out under the action of the torsion spring 90338. When the piston 90319 runs to the corresponding position in the middle of the screw-off cylinder 90341, the pawl 90320 is in fit with the rachet wheel provided inside the power head housing 90306 to form a ratchet-pawl mechanism. Both ends of the screw-off cylinder 90341 are enclosed by the cylinder covers. The high-pressure hydraulic oil is allowed to be injected into the screw-off cylinder 90341 through the oil pipe interface 90340 to push the piston 90319 to move in both two directions, thereby driving the pawl 90320 to move in both directions. When the piston 90319 moves from top to bottom, the pawl 90320 enters the power head housing 90306 and pushes the ratchet wheel 90318 to rotate counterclockwise. Since the piston 90319 is configured to provide a relatively strong thrust. Since the piston 90319 can provide a relatively strong thrust, the power head spindle 90332, which is in key connection to the ratchet wheel 90318, can obtain a relatively large reversing torque, which is much larger than the reversing torque provided by the hydraulic motor 90301, so as to remove the drill pipe that is tightly guarded due to the drilling process. Then the piston 90319 returns, when the piston 90319 is at the uppermost position in FIG. 6, the pawl 90320 automatically retracts into the screw-off cylinder 90341, and the ratchet wheel 90318 and the power head spindle 90332 are allowed to rotate freely in a forward direction and a reverse direction.

The water pump 914 is connected to the flushing joint 918 through the water supply pipe, and the water enters the water through hole inside the jettisoning shaft 90327 under rotating through the flushing joint 918, and then enter the drill pipe 90310 connected to the jettisoning shaft 90327 to form a flushing water flow in the drill hole.

After the drilling operation, the pressure chamber 10 is depressurized, and then the testing platform 9 is transferred out of the pressure chamber 10. The rock core sample is taken out from the coring sleeve 90311. After that, the rock sample block 906 is replaced, and the above steps are repeated to complete a series of core-drilling tests under different drilling pressures and rotational speeds, respectively.

What is claimed is:

1. A micro core-drilling testing system, comprising:
a pressure chamber;
a micro core-drilling testing platform; and
a control device;
wherein the micro core-drilling testing platform is arranged in the pressure chamber; the micro core-drilling testing platform comprises a lower tray, a middle tray, a hydraulic system, a stroke cylinder, a rock sample plate, a rock sample block, a pressure compensation device and a drilling rig; the middle tray is arranged on the lower tray through a plurality of first upright posts; the hydraulic system and the pressure compensation device are arranged on the lower tray; the rock sample plate is supported on the plurality of first upright posts; the rock sample block is fixed on the rock sample plate; the middle tray is provided with a first guide column; the first guide column is vertically provided with a guide chute; the drilling rig is installed on a slide rest; the slide rest is arranged in the guide chute; a lower end of the stroke cylinder is hingedly connected to the middle tray or a bottom of the first guide column, and an upper end of the stroke cylinder is hingedly connected to the slide rest; a drill pipe of the drilling rig is located directly above the rock sample block; the middle tray is provided with a first drill pipe hole corresponding to the drill pipe; the drilling rig, the pressure compensation device and the stroke cylinder are connected to the hydraulic system; and the hydraulic system is connected to the control device.

2. The micro core-drilling testing system of claim 1, wherein the micro core-drilling testing platform further comprises an upper tray; and the upper tray is arranged on the middle tray through a plurality of second upright posts.

3. The micro core-drilling testing system of claim 1, wherein the rock sample block is fixed on the rock sample plate through four clamps; each of the four clamps comprises a bottom plate, a side plate and a reinforcing rib; the bottom plate is fixed on the rock sample plate; the side plate is perpendicularly connected to the bottom plate; the reinforcing rib is provided between the bottom plate and the side plate; and a side surface of the side plate clings to a side surface of the rock sample block.

4. The micro core-drilling testing system of claim 1, wherein a water inlet is provided on a cover at a top of the pressure chamber; the water inlet is connected to an outlet of a pump through a water pipe; an inlet of the pump is connected to a water tank through a pipeline; a top surface of the cover is provided with four first watertight connectors, and a bottom surface of the cover is provided with four second watertight connectors; the four first watertight connectors are respectively electrically connected with the four second watertight connectors; the four second watertight connectors are respectively connected to a temperature sensor, a pressure sensor, a camera and an illumination device; the four first watertight connectors are connected to the control device through a collection device.

5. The micro core-drilling testing system of claim 1, wherein the bottom of the first guide column is provided with a base; the base is screwedly fixed on the middle tray; the lower end of the stroke cylinder is hingedly connected to the base; the base is provided with a second drill pipe hole corresponding to the first drill pipe hole on the middle tray; and a drill bushing is provided at the second drill pipe hole.

6. The micro core-drilling testing system of claim 1, wherein the drilling rig comprises a first hydraulic motor, a power head spindle, a jettisoning shaft, a ratchet wheel and a power head housing; the first hydraulic motor is fixedly provided on a top of the power head housing; the power head housing is fixedly connected to the slide rest; the power head spindle is supported by a first bearing provided inside the power head housing; an upper end of the power head spindle is connected to an output shaft of the first hydraulic motor; the ratchet wheel is fixed on the power head spindle by key joint; the power head housing is provided with a screw-off cylinder corresponding to the ratchet wheel; a pawl groove on a side of a piston rod of the screw-off cylinder is hingedly connected to a pawl through a pawl pin; a torsion spring is provided on the pawl pin; one end of the torsion spring is connected to the pawl, and the other end of the torsion spring is connected to the piston rod of the screw-off cylinder; the pawl is in fit with the ratchet wheel to form a ratchet wheel-pawl mechanism; the screw-off cylinder is connected to the hydraulic system; the power head spindle is sleevedly provided with a jettisoning shaft control sleeve; the jettisoning shaft control sleeve is located inside the power head housing; two hydraulic cavities are formed between the jettisoning shaft control sleeve and an inner wall of the power head housing; the two hydraulic cavities are respectively communicated with two oil ports on the power head housing; the two oil ports are communicated with the hydraulic system to control the jettisoning shaft control sleeve to move along an axis of the power head housing; the jettisoning shaft is arranged in a center hole of the power head spindle; the power head spindle is provided with a plurality of through holes; the plurality of through holes are located in the same plane; a steel ball is provided in each of the plurality of through holes; the jettisoning shaft is provided with a plurality of first grooves respectively corresponding to the plurality of through holes; an upper end surface of each of the plurality of first grooves is tapered; an lower end of the jettisoning shaft control sleeve is provided with a plurality of second grooves, wherein each of the plurality of second grooves is annular; the jettisoning shaft control sleeve is configured to press steel balls respectively into the plurality of first grooves, so as to enable connection of the jettisoning shaft with the power head spindle; when the plurality of second grooves are respectively aligned with the plurality of through holes, the jettisoning shaft is separated from the power head spindle; a lower end of the jettisoning shaft is connected to the drill pipe; and a coring sleeve is provided inside the drill pipe.

7. The micro core-drilling testing system of claim 6, wherein two first sealing rings are arranged between an outer side of the jettisoning shaft control sleeve and an inner side of the power head housing; the bearing comprises a first bearing and a second bearing; an upper end of the power head housing is provided with the first bearing, and a lower end of the power head housing is provided with the second bearing; the first bearing is positioned by an adjusting ring and the ratchet wheel; the adjusting ring is located above the first bearing; an upper end of the adjusting ring is positioned through a lower end of the hydraulic motor; the second bearing is positioned by a power head end cover and a thrust ring; the thrust ring is located inside the power head housing; and an upper end of the thrust ring is positioned by a shaft shoulder on an inner side wall of the power head housing.

8. The micro core-drilling testing system of claim 7, wherein a second sealing ring is arranged between an inner hole of the thrust ring and the jettisoning shaft control sleeve; a third sealing ring is arranged between an outer side of the thrust ring and the power head housing; the second sealing ring and the third sealing ring are both O-shaped; and three oil seals are arranged between the jettisoning shaft and an inner hole of the power head end cover; the pressure compensation device comprises a corrugated pipe, a spring, an upper pressure plate and a base; one end of the corrugated pipe is fixed on the upper pressure plate, and the other end of the corrugated pipe is fixed on the base; the spring is provided inside the corrugated pipe; one end of the spring is connected to the base, and the other end of the spring is connected to the upper pressure plate; the base is provided with a plurality of second guide columns; an axis of each of the plurality of the second guide columns is parallel to an axis of the corrugated pipe; the upper pressure plate is provided with a plurality of guide holes; the plurality of guide holes are sleevedly provided on the plurality of second guide columns, respectively; and an oil port on the base is communicated with the hydraulic system.

9. The micro core-drilling testing system of claim 8, wherein the lower end of the jettisoning shaft is provided with a radial water inlet and an axial water inlet; the radial water inlet is located between two oil seals of the three oil seals; the radial water inlet is communicated with the axial water inlet; the radial water inlet is communicated with a water inlet hole on the power head end cover; a flushing joint is provided at the water inlet hole of the power head end cover; a water pump and a second hydraulic motor are fixed on the rock sample plate; an oil suction port and an oil return port of the second hydraulic motor are connected to the hydraulic system through oil pipes; an output shaft of the second hydraulic motor is connected to the water pump, and a water outlet of the water pump is connected to the flushing joint; and a water suction port of the water pump is connected to a filter through a water pipe.

10. The micro core-drilling testing system of claim 8, wherein the slide rest comprises a main sliding plate, two reinforcing plates, a supporting plate, and a cover plate; the supporting plate is perpendicularly connected to the main sliding plate; the two reinforcing plates are provided between the supporting plate and the main sliding plate; one of the two reinforcing plates is located at a first end of the supporting plate, and the other of the two reinforcing plates is located at a second end of the supporting plate; the supporting plate is provided with a mounting hole; the first hydraulic motor is mounted in the mounting hole; the power head housing is screwedly connected to the main sliding plate; the cover plate is screwedly provided on a surface of the main sliding plate away from the supporting plate; the cover plate is screwedly provided with a sliding connector; and the sliding connector passes through the guide chute to be hingedly connected to a joint of a piston rod of the stroke cylinder.

* * * * *